United States Patent
Choi et al.

(10) Patent No.: US 12,099,058 B2
(45) Date of Patent: Sep. 24, 2024

(54) METHOD FOR QUANTITATIVELY ANALYZING TARGET MATERIAL AND DEVICE FOR QUANTITATIVELY ANALYZING TARGET MATERIAL BY USING SAME

(71) Applicant: SMALL MACHINES, Daejeon (KR)

(72) Inventors: Jun Kyu Choi, Seoul (KR); Gyeong Woo Kang, Seoul (KR)

(73) Assignee: SMALL MACHINES, Seoul (KR)

( * ) Notice: Subject to any disclaimer, the term of this patent is extended or adjusted under 35 U.S.C. 154(b) by 882 days.

(21) Appl. No.: 16/631,703

(22) PCT Filed: Jul. 17, 2017

(86) PCT No.: PCT/KR2017/007651
§ 371 (c)(1),
(2) Date: Jan. 16, 2020

(87) PCT Pub. No.: WO2019/017501
PCT Pub. Date: Jan. 24, 2019

(65) Prior Publication Data
US 2020/0166504 A1 May 28, 2020

(51) Int. Cl.
*G01N 33/543* (2006.01)
*G01N 15/06* (2006.01)
*G01N 15/075* (2024.01)

(52) U.S. Cl.
CPC ... *G01N 33/54326* (2013.01); *G01N 15/0656* (2013.01); *G01N 15/075* (2024.01)

(58) Field of Classification Search
CPC ......... G01N 33/54326; G01N 15/0656; G01N 2015/0693

(Continued)

(56) References Cited

U.S. PATENT DOCUMENTS

| | | | |
|---|---|---|---|
| 2009/0053799 A1* | 2/2009 | Chang-Yen | B03C 1/01 435/306.1 |
| 2010/0128961 A1* | 5/2010 | Kalusche | G06V 20/695 382/133 |

(Continued)

FOREIGN PATENT DOCUMENTS

| KR | 10-2008-0091955 A | 10/2008 |
|---|---|---|
| KR | 10-2013-0111185 A | 10/2013 |

OTHER PUBLICATIONS

Huang et al., Machine Learning Based Single-Frame Super-Resolution Processing for Lensless Blood Cell Counting, Sensors, 2016, vol. 16, pp. 1-16. (Year: 2016).*

(Continued)

*Primary Examiner* — Christopher L Chin
(74) *Attorney, Agent, or Firm* — Sughrue Mion, PLLC

(57) ABSTRACT

The present invention provides a method of quantitatively analyzing a target substance, the method including a step of irradiating a biochip, which includes a plurality of target substances excluding a fluorescence-labeled material, with light; a step of acquiring a plurality of low-resolution images for a region including the plurality of target substances using an image sensor; a step of acquiring a high-resolution image based on the plurality of low-resolution images; and a step of counting the plurality of target substances in the high-resolution image; and a device for quantitatively analyzing a target substance using the method.

9 Claims, 22 Drawing Sheets

(58) Field of Classification Search
USPC .......................................................... 436/526
See application file for complete search history.

(56) References Cited

U.S. PATENT DOCUMENTS

| | | | |
|---|---|---|---|
| 2010/0151447 A1* | 6/2010 | Ely .................... | G01N 33/574 |
| | | | 435/5 |
| 2011/0089942 A1* | 4/2011 | Goodwill ............ | A61B 5/0515 |
| | | | 324/301 |
| 2014/0118529 A1* | 5/2014 | Zheng .................... | G21K 7/00 |
| | | | 348/80 |

OTHER PUBLICATIONS

Zheng et al., Sub-pixel resolving optofluidic microscope for on-chip cell imaging, Lab on a Chip, vol. 10, 2010, pp. 3125-3129. (Year: 2010).*
International Search Report for PCT/KR2017/007651 dated Mar. 27, 2018 [PCT/ISA/210].
Korean Office Action for 10-2018-7024086 dated Jan. 3, 2020.

* cited by examiner

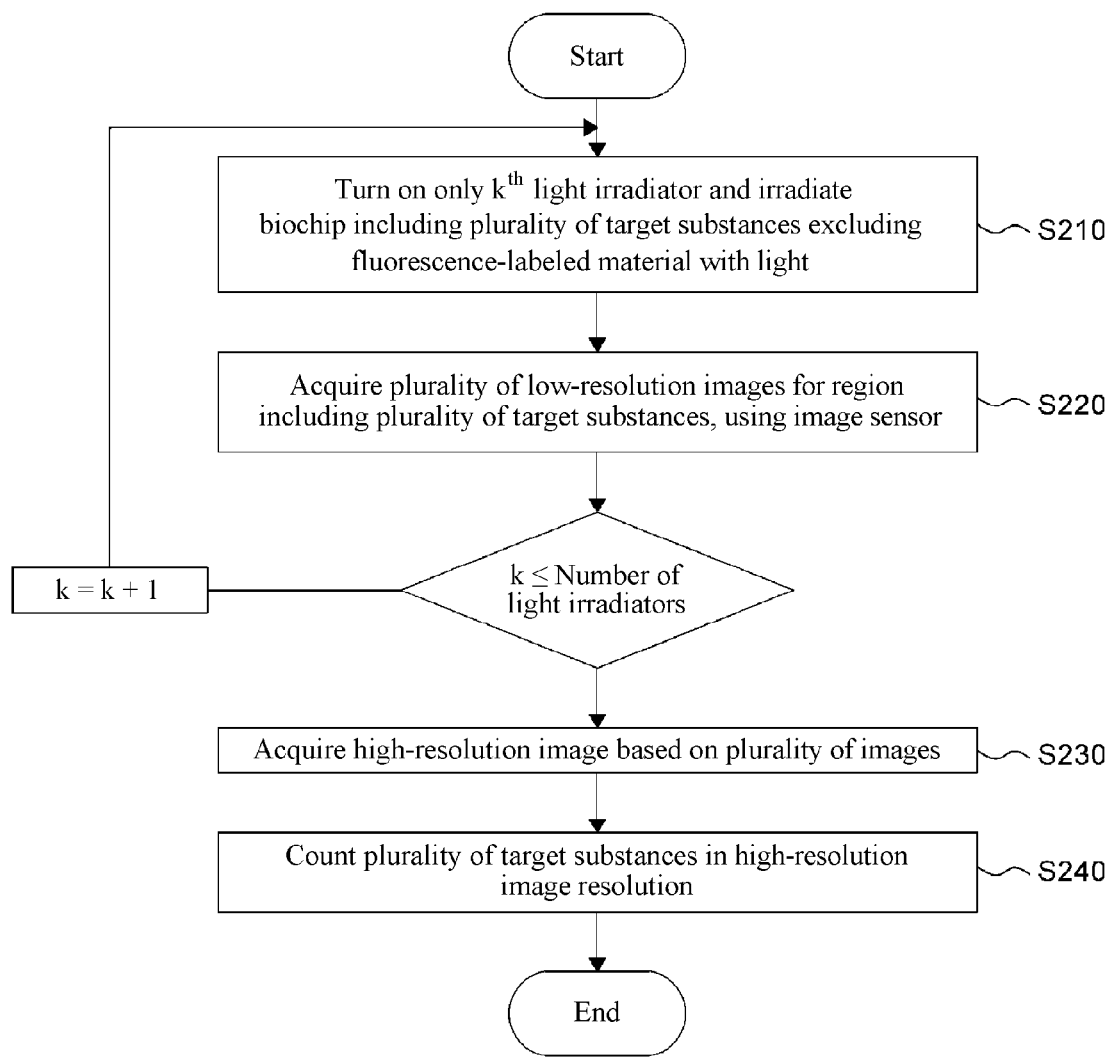

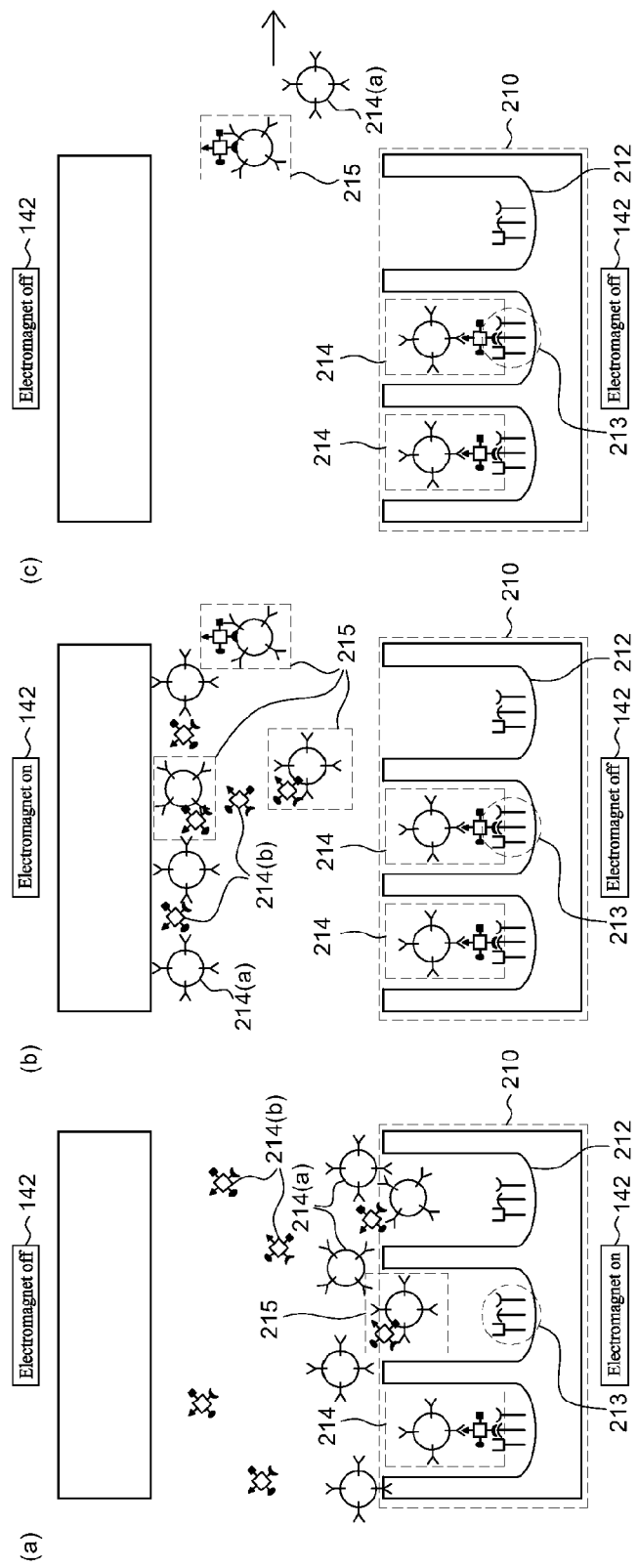

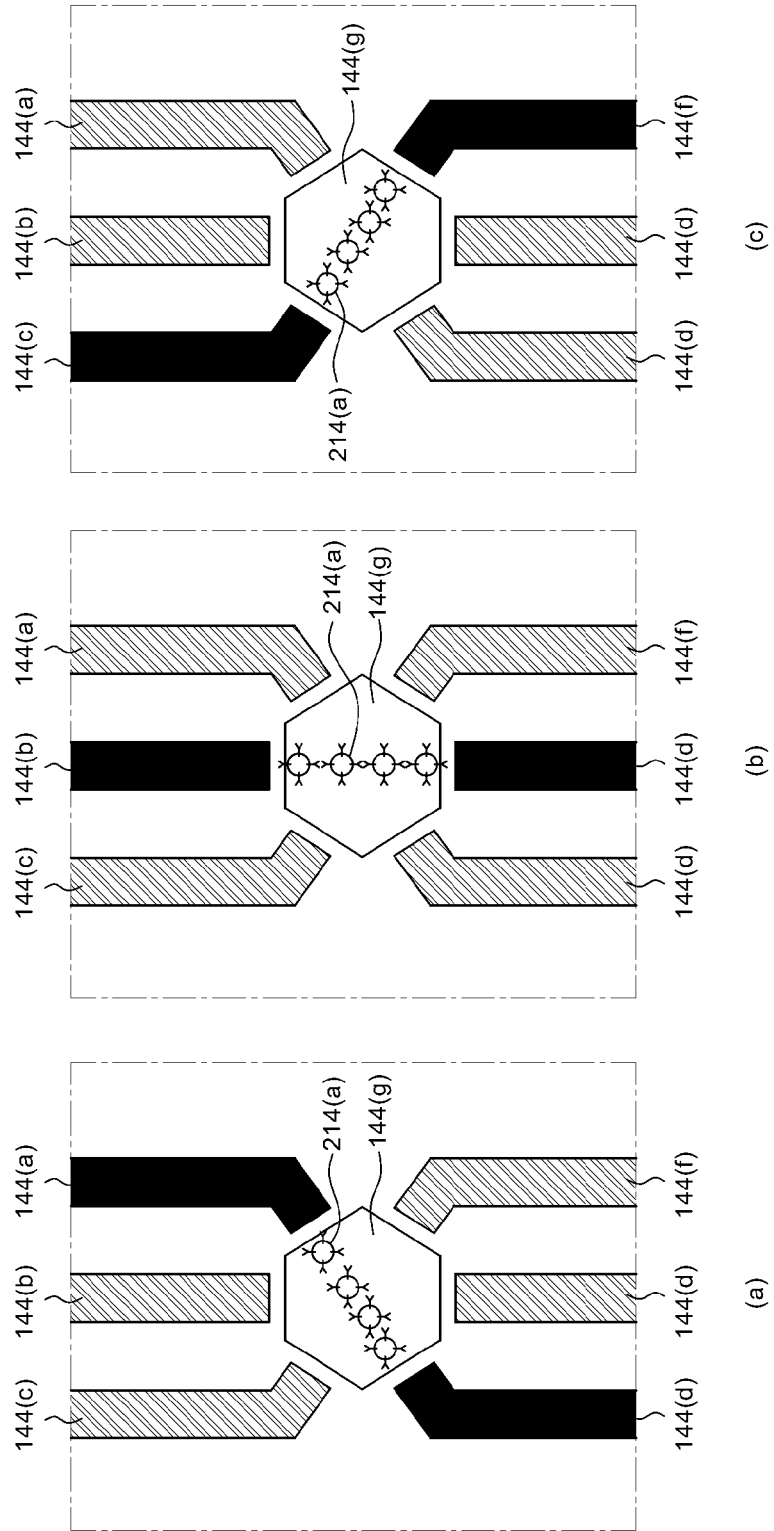

(a)

(b)

METHOD FOR QUANTITATIVELY ANALYZING TARGET MATERIAL AND DEVICE FOR QUANTITATIVELY ANALYZING TARGET MATERIAL BY USING SAME

CROSS REFERENCE TO RELATED APPLICATIONS

This application is a National Stage of International Application No. PCT/KR2017/007651 filed Jul. 17, 2017.

TECHNICAL FIELD

The present invention relates to a method of quantitatively analyzing a target substance and a device therefor, and more particularly to a method of quantitatively analyzing a target substance, which does not include a fluorescence-labeled material, detected in a biochip and a device for quantitatively analyzing the target substance.

BACKGROUND ART

A lab-on-a-chip system refers to a system allowing to carry out laboratory experiments with a single fine chip using the micro-chip semiconductor technology, nanotechnology, and biotechnology. A lab-on-a-chip system-based biochip constituted of microchannels of microliters or nanoliters or less can substitute, using only a trace amount of sample, for experiment or research processes performed in laboratories. In addition, since the lab-on-a-chip system-based biochip is constituted of a multi-channel system, it can perform high-speed parallel processing. Accordingly, biological tests requiring long time and high cost can be carried out at low cost in a short time.

To identify and quantify a target substance detected on a biochip, a mechanical method, a chemical method, an electrical method, methods of detecting a fluorescence amount, light emission light, light absorption amount, or scattered light amount of chemically-treated biochemicals using a light source, and the like may be used. Further, devices equipped with the system may be used. For example, a target substance specifically reacting with a biomaterial labeled with a fluorescent material and, thus, detected in a chip may be quantitatively analyzed based on a fluorescence image of the target substance obtained through an optical detector-based device.

Meanwhile, most biochips may have long rod shapes for smooth flow of assay samples. In most devices used to quantitatively analyze the biochips, a detection resolution to a region exceeds the size of a target substance, so that a single target substance cannot be detected, and the number of target substances is estimated by quantifying an average intensity of signals detected within a specific range. Accordingly, the accuracy of estimates depends on the sensitivity of a detection sensor, and a sensor should be sensitively calibrated to maintain accuracy.

To address the problems, the development of a quantitative analysis device equipped with a high-sensitivity detection sensor has been proposed. However, such a device has a limitation in that it is difficult to solve noise components generated in a sample and a detection environment, and may cause new problems such as complexity of electronic circuits and higher costs.

In addition, an optical magnification adjustment system-based quantitative analysis device, for example a quantitative analysis device adopting a microscope-like manner, developed to improve a detection resolution over an area can detect a single target substance based on some images made by enlarging or reducing target substances. Accordingly, noise, except for a target substance, can be accurately removed, so that even a small amount of target substance can be detected, thereby enabling ultra-high sensitivity quantitative analysis. However, in the case of such a device, it takes a long time for analysis because an area capable of being observed at one time is small, and quantitative analysis results depend upon an optical focus of a target substance.

Therefore, there is a need for development of a novel quantitative analysis method and device capable of providing a highly-reliable quantitative analysis result of a detected target substance.

The background art of the invention has been described to facilitate understanding of the present invention. It should not be understood that the matters described in the background form as prior art of the present invention.

DISCLOSURE

Technical Problem

The present inventors have attempted to develop a novel analysis system that can solve problems such as narrow viewing fields, long analysis times, and high costs of existing optical magnification-based quantitative analysis devices.

As a result, the present inventors have developed a quantitative analysis system using a lensless digital inline microscope based on a complementary metal-oxide semiconductor (CMOS) image sensor. Further, the present inventors have confirmed that a quantitative analysis method and device based on the novel analysis system can provide rapid and accurate quantitative analysis for target substances detected in a biochip.

Therefore, the present invention has been made in view of the above problems, and it is one object of the present invention to provide a method of quantitatively analyzing a target substance based on a CMOS image sensor to provide rapid and accurate quantitative analysis, and a device therefor.

Further, the present inventors have confirmed that target substances can be effectively counted using the quantitative analysis method and device of the present invention that adopt a biochip allowing optical observation of detected target substances, such as a biochip utilizing magnetic particles, without use of a fluorescence-labeled material.

Therefore, it is another object of the present invention to provide a method of quantitatively analyzing a target substance, the method including effectively counting target substances detected in a biochip that excludes a fluorescence-labeled material, and a quantitative analysis device using the method.

More particularly, it is another object of the present invention to provide a method of quantitatively analyzing a target substance, the method including utilizing a magnetic material for applying electromagnetic force such that target substances bound to magnetic particles can be effectively detected in a biochip, and a quantitative analysis device using the method.

It is yet another object of the present invention to provide a method of quantitatively analyzing a target substance, the method including acquiring a plurality of images of target substances and effectively counting a target substance based on a high-resolution image reconstructed based on the acquired images, and a quantitative analysis device using the method.

It will be understood that technical problems of the present invention are not limited to the aforementioned problems and other technical problems not referred to herein will be clearly understood by those skilled in the art from disclosures below.

Technical Solution

In accordance with an aspect of the present invention, the above and other objects can be accomplished by the provision of a method of quantitatively analyzing a target substance, the method including: a step of irradiating a biochip, which includes a plurality of target substances excluding a fluorescence-labeled material, with light; a step of acquiring a plurality of low-resolution images for a region including the plurality of target substances using an image sensor; a step of acquiring a high-resolution image based on the plurality of low-resolution images; and a step of counting the plurality of target substances in the high-resolution image.

According to an aspect of the present invention, the step of irradiating a biochip with light may include a step of irradiating light at a plurality of angles, the step of acquiring a plurality of low-resolution images may include a step of acquiring a plurality of low-resolution shadow images for the region including a shadow image of each of the plurality of target substances generated by light irradiated at the plurality of angles, using a lensless digital inline microscope, the step of acquiring a high-resolution image may include a step of acquiring a high-resolution image including an image of each of the plurality of target substances, based on the plurality of low-resolution shadow images for the region, and the step of counting the plurality of target substances may include a step of counting the plurality of target substances based on the high-resolution image.

According to another aspect of the present invention, the step of acquiring a high-resolution image may include a step of aligning a plurality of shadow images for the region to respectively correspond to the plurality of target substances; and a step of acquiring multilayer images of each of the plurality of target substances reconstructed based on at least one of a pixel value of each of the plurality of shadow images, a wavelength of the predetermined light and a plurality of angles thereof, a distance between the CMOS image sensor and the biochip, and a phase value of each of the plurality of target substances.

According to another aspect of the present invention, the step of acquiring a high-resolution image may further include a step of removing a diffraction pattern of the multilayer images based on at least one of a pixel value of each of the plurality of shadow images, a wavelength of the predetermined light and a plurality of angles thereof, a distance between the CMOS image sensor and the biochip, and a phase value of each of the plurality of target substances.

According to another aspect of the present invention, the step of counting the plurality of target substances may include a step of respectively matching the plurality of target substances in the multilayer images recognized by an align key pattern with predetermined templates; and a step of counting the template-matched target substances.

According to another aspect of the present invention, the light at the plurality of angles may include light at an angle perpendicular to the region, and the step of irradiating a biochip with light may include a step of irradiating the light at the perpendicular angle and light at an angle different from the perpendicular angle.

According to another aspect of the present invention, the light may be non-isotropic light, and the step of irradiating a biochip with light may include a step of irradiating the non-isotropic light through a pinhole aperture so as to irradiate isotropic light.

According to another aspect of the present invention, the biochip may include a detection channel configured to capture the magnetic particle-target substance complexes, a step of applying electromagnetic force through a magnetic material disposed at a position corresponding to the detection channel to capture the magnetic particle-target substance complexes may be further included before the step of irradiating a biochip with light, the step of irradiating a biochip with light may include a step of irradiating the detection channel including the plurality of magnetic particle-target substance complexes with light, and the step of counting the plurality of target substances may include a step of counting the plurality of magnetic particle-target substance complexes in the high-resolution image based on the high-resolution image.

According to another aspect of the present invention, the magnetic material may be disposed on upper and lower parts of the biochip, and the step of applying electromagnetic force through a magnetic material may include a step of only applying electromagnetic force to the magnetic material disposed at a position corresponding to at least one surface of the detection channel; and a step of only applying electromagnetic force to the magnetic material disposed at a position corresponding to another surface of the detection channel.

According to another aspect of the present invention, the biochip may further include a reaction channel connected to the detection channel, a step of applying electromagnetic force through a reaction-inducing magnetic material that is disposed at a position corresponding to the reaction channel configured such that the magnetic particle-target substance complexes are formed therein and includes a plurality of magnetic material pairs may be further included before the step of applying electromagnetic force through a magnetic material, wherein the step of applying electromagnetic force through a reaction-inducing magnetic material includes a step of applying electromagnetic force to a pair of magnetic materials of the plurality of magnetic material pairs disposed at a position corresponding to the reaction channel; and a step of applying electromagnetic force to another pair of magnetic materials closest to the pair of magnetic materials.

In accordance with another aspect of the present invention, there is provided a device for quantitatively analyzing a target substance, the device including a light irradiator configured to irradiate a biochip, which includes a plurality of target substances excluding a fluorescence-labeled material, with light; an image sensor configured to correspond to at least a portion of the light-irradiated biochip and acquire low-resolution images for a region including the plurality of target substances; and a processor configured to align the low-resolution images for the region acquired through the image sensor, acquire a high-resolution image based on reconstructed images for the region, and count the plurality of target substances in the high-resolution image based on the high-resolution image.

According to an aspect of the present invention, the light irradiator may include a plurality of light irradiators, each of the plurality of light irradiators may emit light at different angles, the image sensor may be a CMOS image sensor, and the processor may be configured to align a plurality of shadow images for the region, acquired through the CMOS image sensor, acquire multilayer images of each of the plurality of target substances reconstructed based on at least one of a pixel value of each of the plurality of shadow images, a wavelength of the predetermined light and a plurality of angles thereof, a distance between the CMOS image sensor and the biochip, and a phase value of each of the plurality of target substances, and count the plurality of target substances based on the multilayer images.

According to an aspect of the present invention, the device may further include a plurality of magnetic force applicators for a detection channel which are disposed at a position corresponding to a detection channel configured to capture the magnetic particle-target substance complexes, wherein each of the plurality of magnetic force applicators for a detection channel is disposed at an upper or lower part or upper and lower parts of the biochip.

According to another aspect of the present invention, the plurality of magnetic force applicators for a detection channel may be a movable electromagnet or a transparent PCB electromagnet.

According to another aspect of the present invention, the device may further include a plurality of magnetic force applicators for a reaction channel that are disposed at a position corresponding to a reaction channel connected to the detection channel, wherein each of the plurality of magnetic force applicators for a reaction channel is disposed at an upper or lower part or upper and lower parts of the biochip.

According to another aspect of the present invention, the plurality of magnetic force applicators for a reaction channel may include a plurality of magnetic material pairs, wherein electromagnetic force is sequentially applied to each of the plurality of magnetic material pairs.

According to another aspect of the present invention, the light irradiator may include a pinhole aperture to emit isotropic light, wherein the pinhole aperture has a diameter of 0.5 to 2.5 μm.

According to another aspect of the present invention, the light irradiator may further include a wavelength filter.

According to another aspect of the present invention, the light irradiator may be disposed at an interval of 30 to 150 mm from the biochip, and the image sensor may be disposed at an interval of 0.02 to 3 mm from the biochip.

According to another aspect of the present invention, when the light irradiator is disposed at an interval of 30 to 150 mm from the biochip and the image sensor is disposed at an interval of 0.02 to 3 mm from the biochip, a resolution of the high-resolution image may be 0.3 to 0.7 μm.

Advantageous Effects

Since the present invention uses a lensless digital inline microscope, a method of quantitatively analyzing a target substance and a quantitative analysis device using the method according to the present invention can provide a wide analysis region for a biochip in which a target substance is detected.

Accordingly, the present invention can rapidly perform quantitative analysis for a target substance detected in a biochip.

In addition, the present invention can acquire a plurality of images for a specific region of a biochip including target substances and count the target substances based on a high-quality image reconstructed based on the plurality of images, thereby being capable of providing accurate quantitative analysis.

More particularly, since the present invention uses a magnetic material for applying electromagnetic force, the detection efficiency of target substances can be increased and the detected target substances can be effectively counted using a biochip including magnetic particles to optically observe detected target substances, without use of a fluorescence-labeled material.

Effects according to the present invention are not limited by those exemplified above, and more various effects are included in the present specification.

DESCRIPTION OF DRAWINGS

FIG. 2A illustrates a procedure of a method of quantitatively analyzing a target substance according to an embodiment of the present invention.

FIG. 2G illustrates enlarged views of a main part of a detection channel of a biochip so as to describe a step of applying electromagnetic force in a method of quantitatively analyzing a target substance according to an embodiment of the present invention.

FIG. 2I illustrates enlarged views of a main part of a reaction channel of a biochip so as to describe a step of applying electromagnetic force in a method of quantitatively analyzing a target substance according to an embodiment of the present invention.

MODES OF THE INVENTION

Figure 1A:
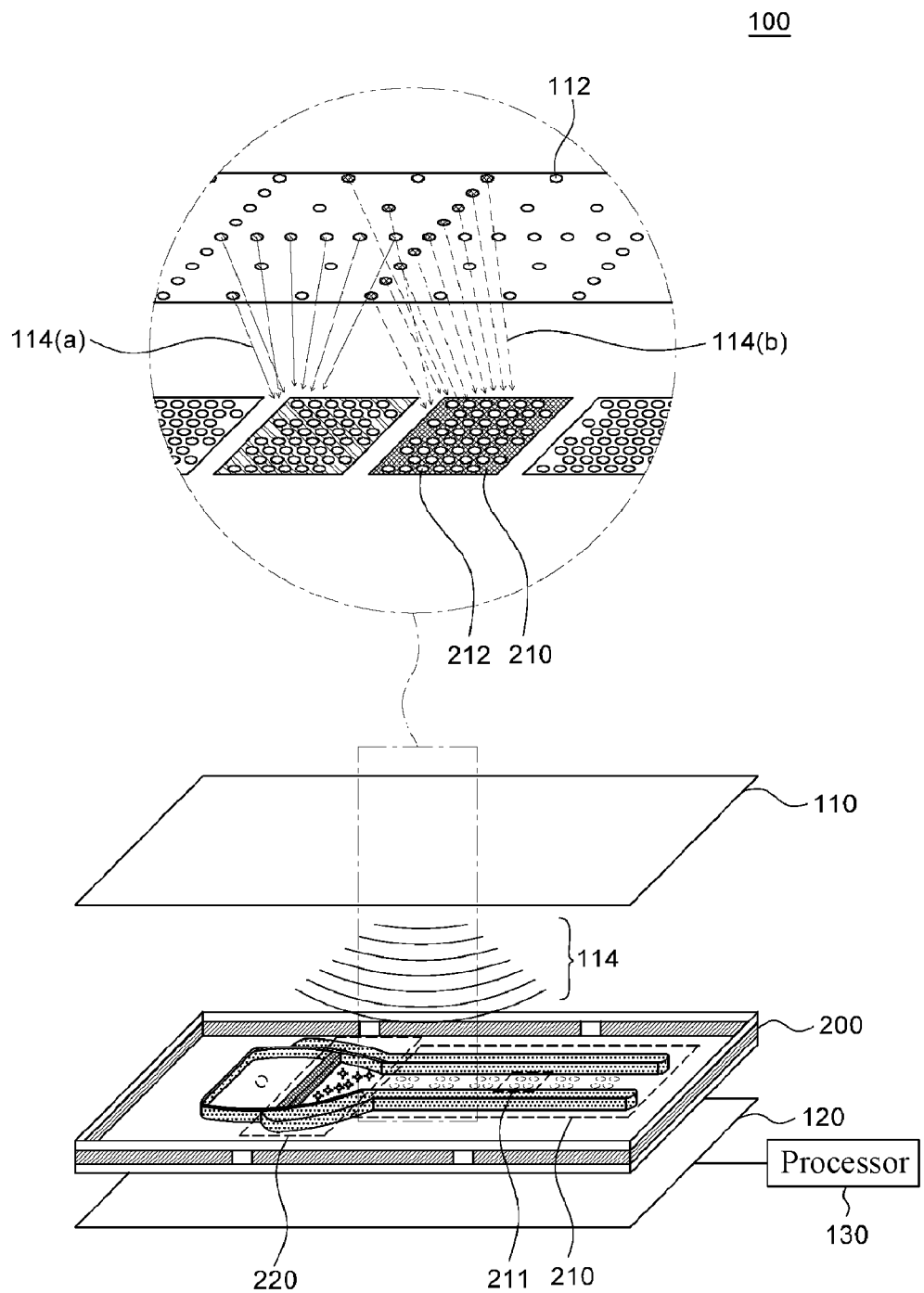
FIG. 1A is a schematic exploded perspective view illustrating the configuration of a device for quantitatively analyzing a target substance according to an embodiment of the present invention.

The attached drawings for illustrating exemplary embodiments of the present invention are referred to in order to gain a sufficient understanding of the present invention, the merits thereof, and the objectives accomplished by the implementation of the present invention. The invention may, however, be embodied in many different forms and should not be construed as being limited to the embodiments set forth herein; rather, these embodiments are provided so that this disclosure will be thorough and complete, and will fully convey the concept of the invention to one of ordinary skill in the art. Meanwhile, the terminology used herein is for the purpose of describing particular embodiments and is not intended to limit the invention.

The shapes, sizes, ratios, angles, numbers, and the like disclosed in drawings for describing embodiments of the present invention are exemplary, and thus, the present invention is not limited to the illustrated particulars. In addition, in the following description of the present invention, a detailed description of known functions and configurations incorporated herein will be omitted when it may make the subject matter of the present invention unclear. In expressions "comprise", "have", "consist of" and the like mentioned in the present specification, other parts may be added unless 'only' is used. Singular forms "a," "an" and "the" are intended to include the plural forms as well, unless the context clearly indicates otherwise.

In interpreting components, it is interpreted to include error ranges even if there is no separate description.

Each of the features of the various embodiments of the present invention may be combined with each other in part or in whole, various interlocking and driving are allowed as can be understood by those skilled in the art, and each of embodiments may be implemented independently or together in combined forms.

For clarity of interpretation of the present specification, the terms used herein will be defined below.

The term "target substance" used in the specification may include an antigen or a nuclear protein acting as an antigen. However, a target substance may be easily selected by a user according to the type of biochip. For example, in the case of a biochip using magnetic particles, a target substance may be a complex composed of a magnetic particles-target substance.

Further, the target substance may be an antibody against influenza A, influenza B, respiratory syncytial virus (RSV), parainfluenza virus-1, parainfluenza virus-2, parainfluenza virus-3, adenovirus, human metapneumovirus (hMPV) or rhinovirus (1, 2). In addition, when an allergy test is to be performed using the microchip for analyzing fluids according to an embodiment of the present invention, a detection target substance may be IL-1 beta, IL-10, IL-2, IL-4, IL-5, IL-6, IL-71, IFN gamma, TNF-α or GM-CSF. Further, when an acute myocardial infarction diagnostic test is to be performed using the microchip for analyzing fluids according to an embodiment of the present invention, a detection target substance may be troponin I, BNP, high-sensitivity (hs) CRP, CK-MB, D-dimer, or myoglobin. Furthermore, when a sexually transmitted disease test is to be performed using the microchip for analyzing fluids according to an embodiment of the present invention, a detection target substance may include human immunodeficiency virus (HIV), *chlamydia* bacteria, *Treponema pallidum*, gonococcus (*Neisseria gonorrhoeae*), or human papilloma virus (HPV). When a prostate cancer test is to be performed using a biochip, a target substance may be a prostate specific antigen (PSA). In addition, when an immunity test of a transplantation patient is to be performed using a biochip, a target substance may be a BK virus or cytomegalovirus (CMV) antigen. However, a target substance is not limited to those listed above, and a target substance may include various types of cells to be counted.

The term "fluorescence-labeled material" used in the specification refers to a labeled material to which a fluorochrome generating fluorescence by light stimulation is bound. A fluorescent pigment may be generally fluorochromic isothiocyanate (FITC), rhodamineisothiocyanate (RITC) emitting red fluorescence, or a pigment protein of phycoerythrin. To identify and count target substances detected in conventional biochips, it may be essential to use a fluorescence-labeled material. Accordingly, in the case of conventional methods of quantitatively analyzing a target substance and conventional devices therefor, a fluorescence antibody method, flow cytometry, and an immunofluorescence method are used to identify signals for a fluorescence-labeled antibody that has been subjected to an antigen-antibody reaction, thereby indirectly identifying a target substance.

The term "quantitative analysis" used in the specification refers to an analysis method of clarifying a quantitative relationship in a substance. According to another embodiment of the present invention, a method of quantitatively analyzing a target substance and a device therefor are provided. For example, in accordance with a method of quantitatively analyzing a target substance according to another embodiment of the present invention and a device therefor using a microchip for analyzing fluids according to an embodiment of the present invention, a detection target antigen may be detected and quantitatively analyzed by counting magnetic particles having a countable size captured in a detection channel in a biochip.

The term "CMOS image sensor" used in the specification may refer to a low power consumption-type image sensing device having a complementary metal oxide semiconductor structure. A lensless digital inline microscope based on a CMOS image sensor may be used in the method of quantitatively analyzing a target substance and the device therefor according to an embodiment of the present invention. Here, the device for quantitatively analyzing a target substance based on the lensless digital inline microscope may exhibit improved analysis performance, compared to existing quantitative analysis devices. More particularly, quantitative analysis devices based on an optical magnification adjustment system may perform quantitative analysis for a target substance based on some fluorescent images made by enlarging or reducing the target substance, so that it takes a long analysis time and a quantitative analysis result may be changed according to the focus of the target substance.

Meanwhile, when a biochip is introduced into the quantitative analysis device according to an embodiment of the present invention based on a CMOS image sensor, images of a target substance captured in the biochip may be rapidly obtained by the CMOS image sensor. In addition, the obtained image may be reconstructed into a high-resolution image according to the quantitative analysis method according to an embodiment of the present invention. As a result, the method of quantitatively analyzing and the device therefor according to an embodiment of the present invention may provide an accurate counting result of a target substance.

The term "magnetic particles" used in the present specification refers to particles having magnetic properties. The magnetic particles may be attached to a biochip used in the method of quantitatively analyzing a target substance and the device therefor according to an embodiment of the present invention.

Here, magnetic particles may be optically counted and may have a size where nonspecific self-assembly does not occur. For example, when a particle diameter of the magnetic particles is 0.1 to 6.0 µm, the magnetic particles may be optically counted even if an antibody is not a fluorescence-labeled antibody. Further, magnetic particles having a particle diameter of 0.1 to 6.0 µm have a lower probability of nonspecific self-assembly than magnetic particles having a particle diameter of 0.1 µm or less.

The term "magnetic force applicator" used in the specification may refer to any material capable of forming magnetism with magnetic particles in a biochip. For example, a magnetic material may be used to promote an antigen-antibody reaction in a reaction channel inside a biochip or to accurately, quantitatively analyze a target substance captured in a detection channel. In particular, the magnetic material may be an electromagnet whose magnetization is adjustable, and the biochip may be introduced between two electromagnets disposed in the quantitative analysis device according to an embodiment of the present invention. As the magnetic force of the two electromagnets is adjusted, nonspecific immune complexes or magnetic particles, which do not react with a target antigen, in the biochip may be washed out, resulting in highly accurate quantitative analysis of a target antigen.

Meanwhile, the term "electromagnetic force applicator" used in the specification may be used as the same meaning as the aforementioned "magnetic material." For example, the quantitative analysis device according to an embodiment of the present invention may also include a magnetic force applicator. The magnetic force applicator may include an electromagnetic force applicator for a reaction channel, wherein the electromagnetic force applicator is constituted of a plurality of magnetic material pairs and disposed to correspond to a reaction channel of a biochip; and an electromagnetic force applicator for a detection channel, wherein the electromagnetic force applicator is disposed to correspond to a detection channel of the biochip. Here, the electromagnetic force applicators may have various shapes so long as they can apply electromagnetic force to a reaction channel or a detection channel.

Hereinafter, the device for quantitatively analyzing a target substance according to an embodiment of the present invention is described in detail with reference to FIGS. 1A to 1I.

Figure 1B:
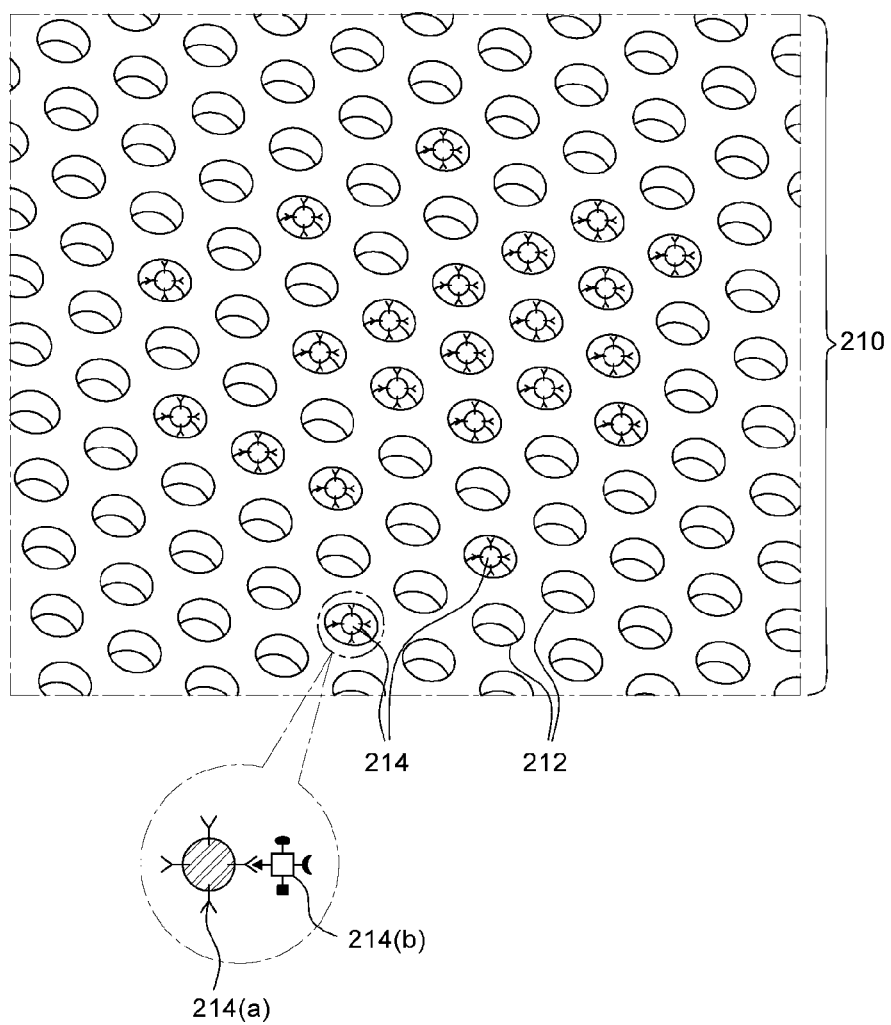
FIG. 1B exemplarily illustrates an area to be analyzed of a biochip introduced into a device for quantitatively analyzing a target substance according to an embodiment of the present invention.
Figure 1C:
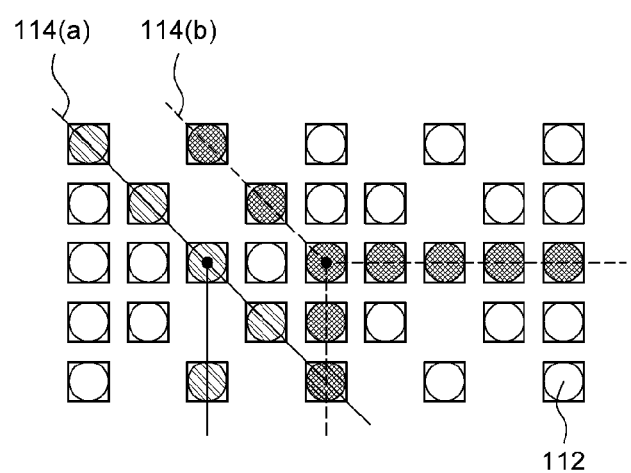
FIG. 1C exemplarily illustrates a light irradiator in a device for quantitatively analyzing a target substance according to an embodiment of the present invention.
Figure 1D:
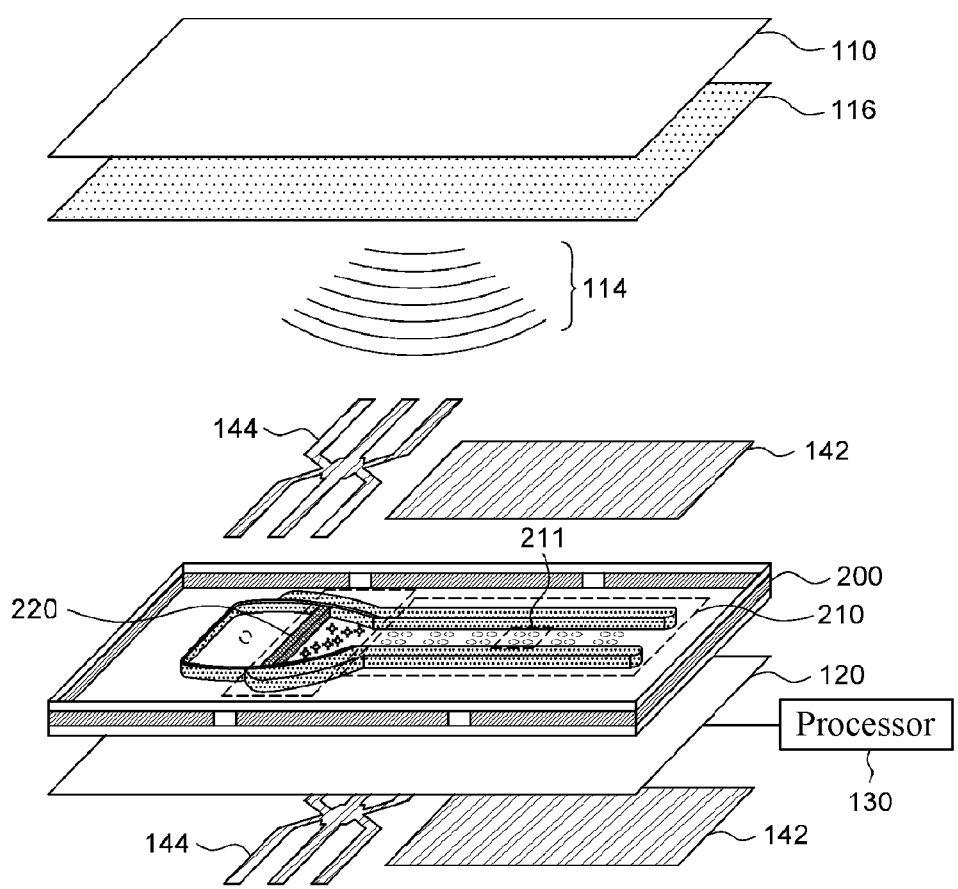
FIG. 1D is a schematic exploded perspective view illustrating the configuration of a device for quantitatively analyzing a target substance according to an embodiment of the present invention.

FIG. 1A is a schematic exploded perspective view illustrating the configuration of a device for quantitatively analyzing a target substance according to an embodiment of the present invention. FIG. 1B exemplarily illustrates an area to be analyzed of a biochip introduced into a device for quantitatively analyzing a target substance according to an embodiment of the present invention. FIG. 1C exemplarily illustrates a light irradiator in a device for quantitatively analyzing a target substance according to an embodiment of the present invention. FIG. 1D is a schematic exploded perspective view illustrating the configuration of a device for quantitatively analyzing a target substance according to an embodiment of the present invention.

Referring to FIG. 1A, a quantitative analysis device 100 includes a light irradiator 110, an image sensor 120 and a processor 130. Here, a biochip 200 in which a target substance has been detected may be disposed between the light irradiator 110 and the image sensor 120. Meanwhile, the biochip 200 introduced into the quantitative analysis device 100 may include a detection channel 210 and a reaction channel 220. The detection channel 210 may include a plurality of detection regions 211. Here, a target substance captured in the detection channel 210 of the biochip 200 may be a magnetic particle-target antigen complex generated by an immune response with magnetic particles.

For example, referring to FIG. 1B, each of the detection regions 211 may include a plurality of holes 212. In the holes 212, magnetic particle-target antigen complexes 214 formed by an immune response between magnetic particles 214(*a*) and target antigens 214(*b*) may be captured. Here, since the magnetic particle-target antigen complexes 214 may have a size that is optically countable, the target antigens 214(*b*) may be quantitatively analyzed by counting the magnetic particle-target antigen complexes 214 even if the biochip 200 does not include a fluorescence-labeled material.

Referring to FIG. 1A, the light irradiator 110 includes a plurality of LEDs 112, wherein the LEDs 112 are configured to irradiate specific detection regions 211 with light. Referring to FIG. 1C, about 10 to 20 LEDs 112 constituting the light irradiator 110 may be configured to irradiate specific detection regions 211 with light. For example, detection regions 211 irradiated with light 114 (*a*) may be different from those irradiated with light 114 (*b*). Here, the respective LEDs 112 may be arranged at an interval of 3 mm and configured to irradiate at various angles including an angle perpendicular to the detection regions 211. For example, when the LEDs 112 are arranged at 0° perpendicular to the detection regions 211, ±2.5°, ±3.5°, ±4.9°, ±6.9°, all of the detection regions 211 in the biochip 200 may be constantly irradiated with light 114 using a small number of the LEDs 112. As a result, high-resolution images of the detection regions 211 may be obtained. Here, the light 114 may be preferably isotropic light. In addition, light at various wavelengths may be radiated according to a target substance to be analyzed. Meanwhile, the number and angle of the LEDs 112 in the light irradiator 110 may be variously set according to the size or configuration of the biochip 200 or the type of target substance.

The image sensor 120 may detect target substances in the detection regions 211 as the light 114 is irradiated through the light irradiator 110. As a result, images of the target substances may be obtained. For example, a plurality of low-resolution images, generated by irradiating with the light 114 at a plurality of angles, of the magnetic particle-target antigen complexes 214 in the detection regions 211 may be obtained through the image sensor 120. Here, the image sensor 120 may be a CMOS image sensor or a lensless digital inline microscope based on a CMOS image sensor, but the present invention is not limited thereto.

The processor 130 may be configured to be connected to the image sensor 120 and, accordingly, may count target substances in the obtained images of the detection regions 211. For example, high-resolution images may be obtained based on a plurality of low-resolution images of the detection regions 211 including the magnetic particle-target antigen complexes 214 obtained through the image sensor 120 of the processor 130, and magnetic particle-target antigen complexes 214 in the high-resolution images may be counted.

Referring to FIG. 1D, the light irradiator 110 of the quantitative analysis device 100 may further include a pinhole aperture 116. For example, when irradiated light 114 is not isotropic light, the light irradiator 110 may include the pinhole aperture 116 to irradiate isotropic light. Here, the diameter of pinholes in the pinhole aperture 116 may be 0.5 to 2.5 μm, but the present invention is not limited thereto. Optionally, the light irradiator 110 may further include a wavelength filter.

Further, the quantitative analysis device 100 may further include an electromagnetic force applicator. Here, a plurality of electromagnetic force applicators may be provided to effectively apply electromagnetic force to a biochip. For example, the electromagnetic force applicator may include electromagnetic force applicators 142 for a detection channel that are configured to apply electromagnetic force to a detection channel of the biochip 200; and electromagnetic force applicators 144 for a reaction channel that are configured to apply electromagnetic force to a reaction channel. The electromagnetic force applicators 142 and 144 may be on each of upper and lower surfaces of the biochip 200. Further, the electromagnetic force applicators 142 and 144 may be transparent PCB electromagnets through which the biochip 200 is irradiated with the light 114, or a moveable electromagnets. In particular, the electromagnetic force applicators 142 for a detection channel may be electromagnets with a circular gradient to effectively apply electromagnetic force for quantitative analysis of the magnetic particle-target antigen complexes 214, but the present invention is not limited thereto.

Figure 1E:
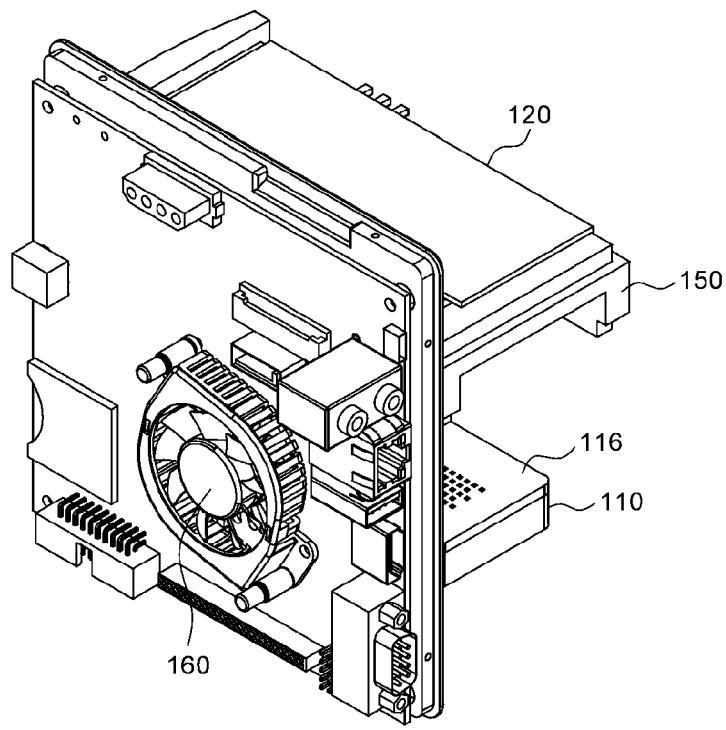
FIGS. 1E to 1i are schematic perspective views illustrating a device for quantitatively analyzing a target substance according to one exemplary embodiment of the present invention.
Figure 1F:
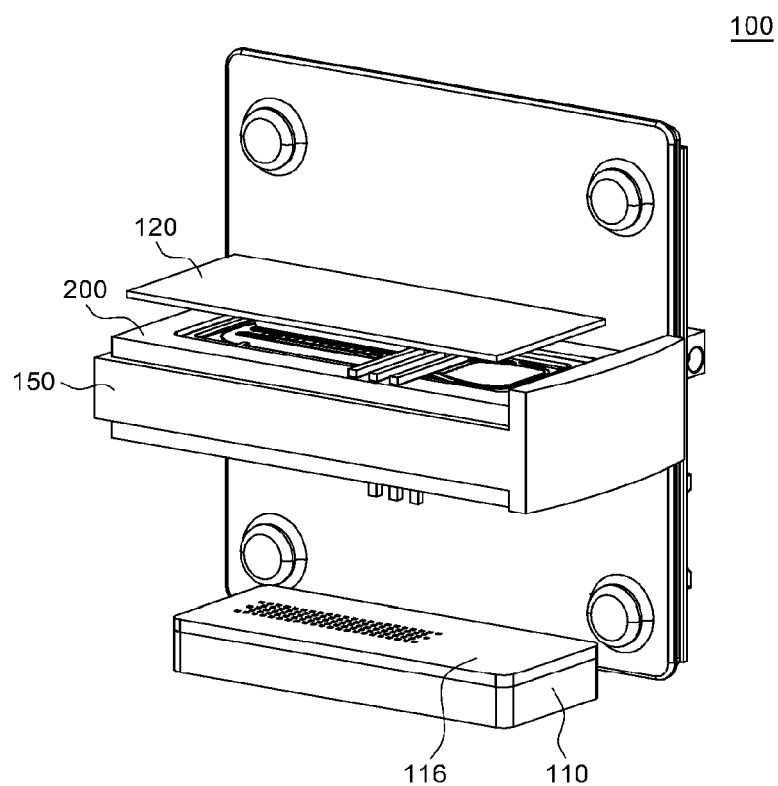
Figure 1G:
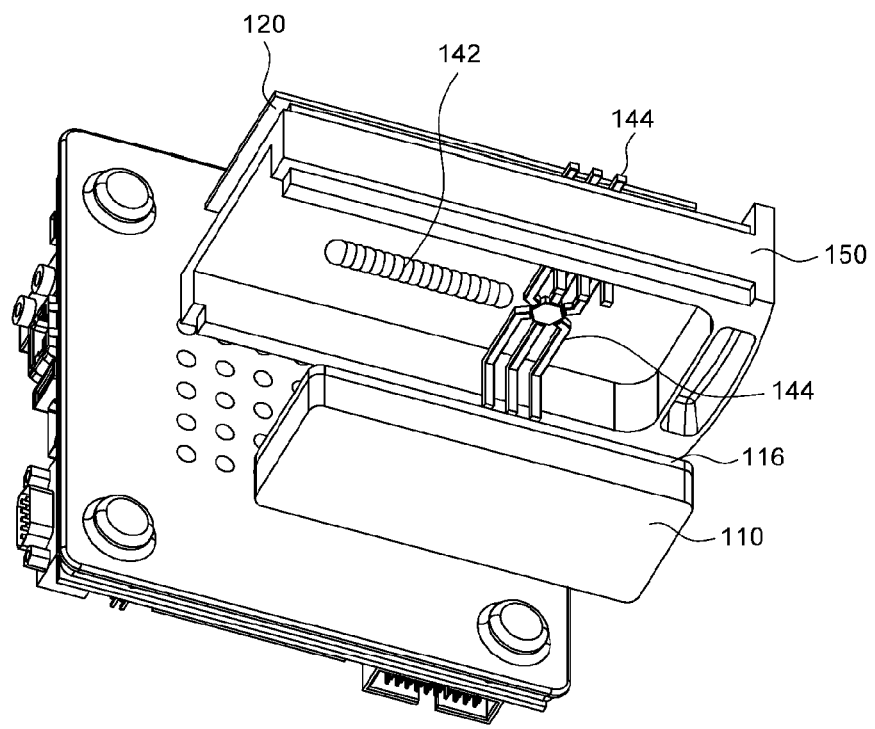
Figure 1H:
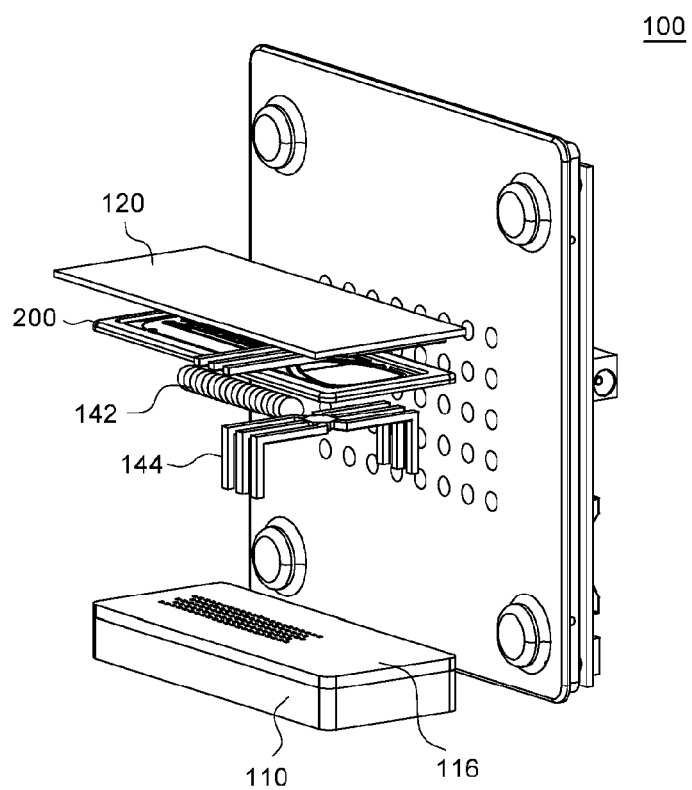
Figure 1I:
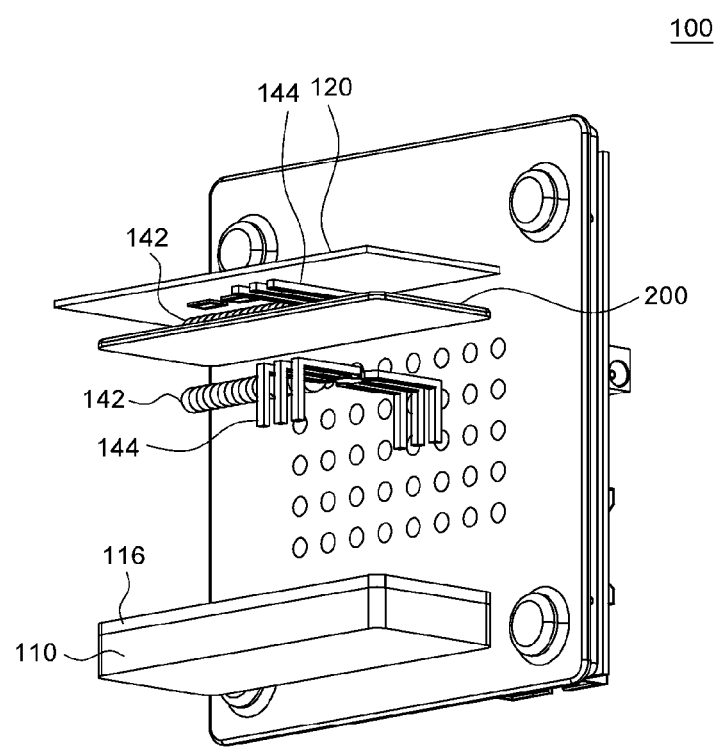

FIGS. 1E to 1I illustrate perspective views of the quantitative analysis device 100 according to one exemplary embodiment of the present invention. Referring to FIG. 1E, the quantitative analysis device 100 may further include a main board 160 for setting the driving or execution thereof and maintaining data such as image data and counting data of a target substance. Further, referring to FIGS. 1E to 1G, a biochip introducer 150 for stably introducing the biochip 200 into the quantitative analysis device 100 may be further included. In particular, the electromagnetic force applicators 142 and 144 may be disposed on an upper surface of the biochip 200 and a lower surface of the biochip introducer 150 to apply electromagnetic force to the biochip 200, and the light irradiator 110 may be disposed on a lower surface of the biochip 200 to irradiate the light 114 from below to upward. Further, the image sensor 120 may be disposed on an upper surface of the biochip 200 to acquire an image generated as the biochip 200 is irradiated with the light 114 through the light irradiator 110. FIGS. 1H and 1I illustrate perspective views of the quantitative analysis device 100 excluding the biochip introducer 150. More particularly, the electromagnetic force applicators 142 for a detection channel may be electromagnets with a circular gradient to effectively apply electromagnetic force to the detection regions 211, as described above. Further, the electromagnetic force applicators 144 for a reaction channel may have a shape composed of a core magnetic material and protruding magnetic materials surrounding the core magnetic material so as to optionally apply electromagnetic force. Meanwhile, to effectively irradiate the light 114 and obtain a high-resolution image of a target substance, a distance between the light irradiator 110 and the biochip 200 may be longer than a distance between the image sensor 120 and the biochip 200. For example, when the light irradiator 110 is disposed at intervals of 30 to 150 mm with the biochip 200 and the image sensor 120 is disposed at intervals of 0.02 to 3 mm with the biochip 200, the resolution of a target substance image obtained through the image sensor 120 may be 0.3 to 0.7 μm. As a result, an analysis range of the quantitative analysis device 100 according to an embodiment of the present invention may be 72 mm$^2$. Components of the quantitative analysis device 100 and the characteristics thereof are not limited to those described above, and the respective components of the quantitative analysis device 100 may be variously arranged and have more wider variety of shapes so long as they can provide high-resolution images and a wide analysis range for the detection regions 211 of the biochip 200.

Figure 2B:
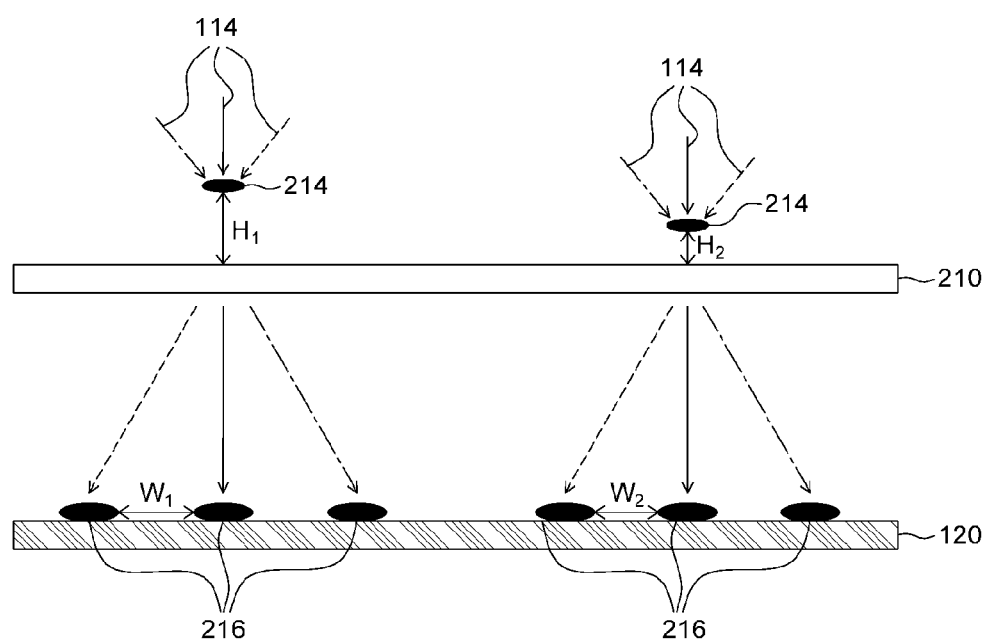
FIG. 2B exemplarily illustrates a step of acquiring a low-resolution image in a method of quantitatively analyzing a target substance according to an embodiment of the present invention.
Figure 2C:
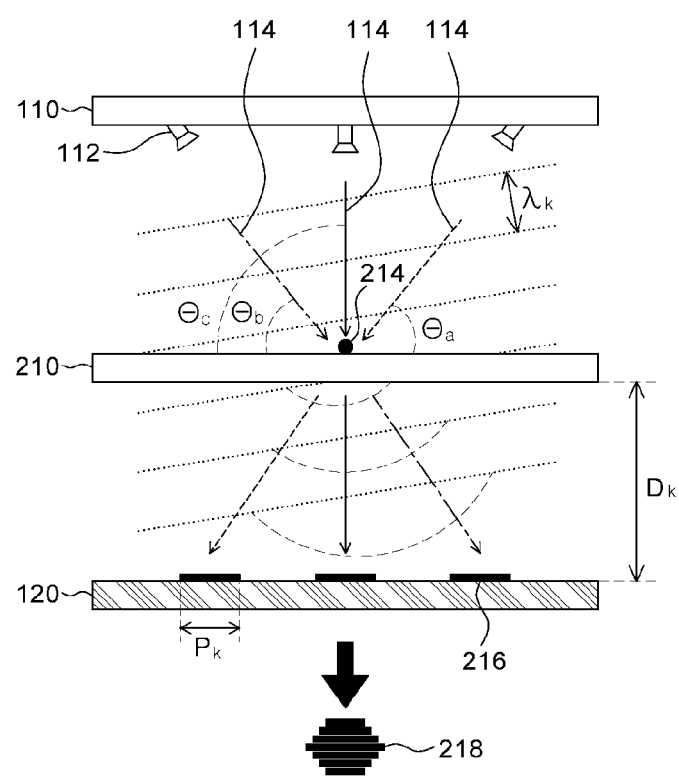
FIGS. 2C and 2D exemplarily illustrate a step of acquiring a high-resolution image in a method of quantitatively analyzing a target substance according to an embodiment of the present invention.
Figure 2D:
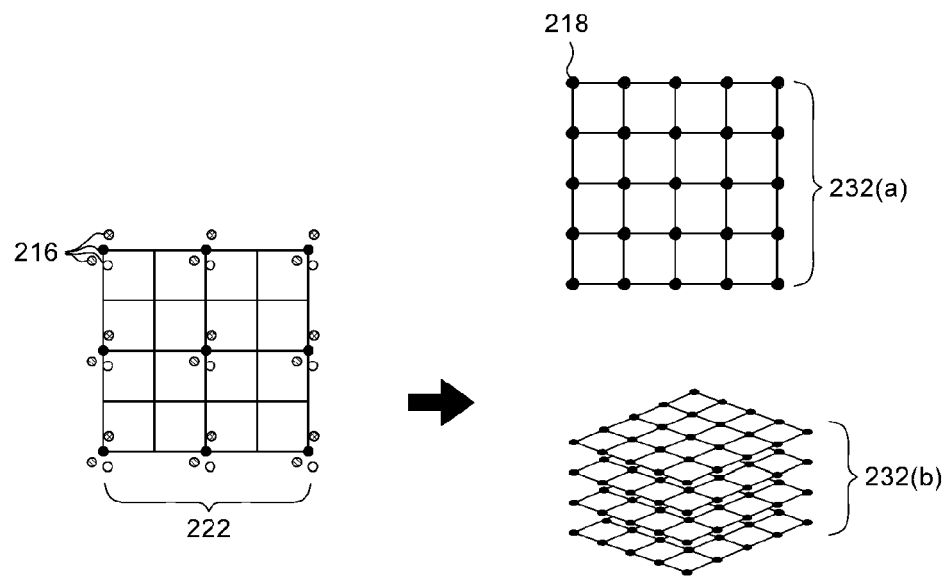
Figure 2E:
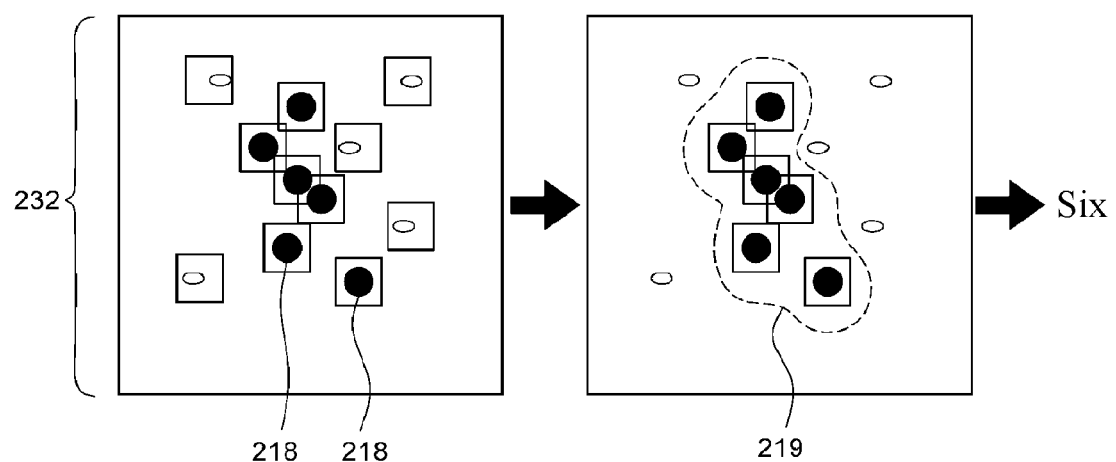
FIG. 2E exemplarily illustrates a step of counting a target substance in a method of quantitatively analyzing a target substance according to an embodiment of the present invention.

Hereinafter, the method of quantitatively analyzing a target substance according to an embodiment of the present invention is described in detail with reference to FIGS. 2A to 2D. Here, reference numerals used in FIGS. 1A to 1I are used to refer to components for convenience of description. FIG. 2A illustrates a procedure of a method of quantitatively analyzing a target substance according to an embodiment of the present invention. FIG. 2B exemplarily illustrates a step of acquiring a low-resolution image in a method of quantitatively analyzing a target substance according to an embodiment of the present invention. FIGS. 2C and 2D exemplarily illustrate a step of acquiring a high-resolution image in a method of quantitatively analyzing a target substance according to an embodiment of the present invention. FIG. 2E exemplarily illustrates a step of counting a target substance in a method of quantitatively analyzing a target substance according to an embodiment of the present invention.

Referring to FIG. 2A, the method of quantitatively analyzing a target substance according to an embodiment of the present invention may include a step (S210) of irradiating a biochip, which includes a plurality of target substances excluding a fluorescence-labeled material, with light; a step (S220) of acquiring a plurality of low-resolution images for a region including the plurality of target substances using an image sensor; a step (S230) of acquiring a high-resolution image based on the plurality of low-resolution images; and a step (S240) of counting the plurality of target substances in the high-resolution image.

In particular, in the step (S210) of irradiating a biochip with light, target substances detected in the biochip 200 may be irradiated with the light 114 by the light irradiators 110 disposed at a plurality of angles. For example, in the step (S210) of irradiating a biochip with light, a specific detection region 211 may be irradiated with the light 114 as a k$^{th}$ light irradiator 110 of the plurality of light irradiators 110 is turned on. Here, the k value is increased by the number of the light irradiators 110 and, as a result, the detection regions 211 may be sequentially irradiated with the light 114. Meanwhile, referring to FIG. 2B, as the magnetic particle-target antigen complex 214 present in the detection channel 210 is irradiated with the light irradiators 110 set at multiple angles, plural shadows 216 of the magnetic particle-target antigen complex may be generated. Accordingly, images of the magnetic particle-target antigen complex shadows 216 generated by irradiating with the light 114 at a plurality of angles may be formed on the image sensor 120. Here, intervals W between the magnetic particle-target antigen complex shadows 216 may be different depending upon the position or height (H) of the magnetic particle-target antigen complexes 214 captured in the detection channel 210. For example, when the magnetic particle-target antigen complex 214 is located at position $H_1$ spaced from the detection channel 210, the interval, $W_1$, between the magnetic particle-target antigen complex shadows 216 may be wider than the interval, $W_2$, between the magnetic particle-target antigen complex shadows 216 located at position $H_2$. That is, the interval W between the magnetic particle-target antigen complex shadows 216 generated on the image sensor 120 may be proportionally widened as the magnetic particle-target antigen complex 214 is located at a higher position (H) from the detection channel 210.

In the step (S220) of acquiring low-resolution images, low-resolution images of target substances may be obtained through the image sensor 120. For example, in the step (S220) of acquiring low-resolution images, a plurality of shadow images of the detection regions 211 which are generated by irradiating light with the light irradiators 110 located at a $k^{th}$ position through the image sensor 120 may be acquired. As a result, a plurality of low-resolution shadow images including shadow images of the magnetic particle-target antigen complexes 214 in the detection regions 211 may be acquired. Here, in the step (S220) of acquiring low-resolution images, low-resolution images of the detection regions 211 may be sequentially acquired by the light 114 sequentially irradiated at various positions as the k value increases. When the k value becomes larger than the number of the light irradiators 110, the step (S220) of acquiring low-resolution images is finished, and the step (S230) of acquiring a high-resolution image, as a subsequent step, proceeds.

In the step (S230) of acquiring a high-resolution image, a high-resolution image may be acquired based on the plurality of low-resolution images of the target substances acquired in the step (S220) of acquiring low-resolution images. For example, referring to FIG. 2D, in the step (S230) of acquiring a high-resolution image, the plurality of shadow images acquired in the step (S220) of acquiring low-resolution images may be acquired as a low-resolution image 222 aligned to correspond to the magnetic particle-target antigen complexes 214. In addition, a high-resolution image 232, which includes magnetic particle-target antigen complexes 218, reconstructed based on a pixel value ($P_a$) of each of the magnetic particle-target antigen complex shadows 216 in FIG. 2C, the wavelength ($\lambda_k$) of the light 114, a plurality of angles ($\theta_a$, $\theta_b$, $\theta_c$) at which the plurality of LEDs 112 are respectively irradiated, and an interval ($D_k$) between the image sensor 120 and the biochip 200 (or the detection channel 210) may be acquired. Here, the high-resolution image 232 consists of multilayer images including the magnetic particle-target antigen complexes 214 (see 232(a) and 232(b)). Optionally, in the step (S230) of acquiring a high-resolution image, the high-resolution image 232 from which a diffraction pattern has been removed may be acquired based on a pixel value ($P_a$) of each of the magnetic particle-target antigen complex shadows 216, the wavelength ($\lambda_k$) of the light 114, a plurality of angles ($\theta_a$, $\theta_b$, $\theta_c$) at which the plurality of LEDs 112 are respectively irradiated, and an interval ($D_k$) between the image sensor 120 and the biochip 200 (or the detection channel 210).

Finally, in the step (S240) of counting the plurality of target substances, the target substance may be counted based on the high-resolution image 232 acquired in the step (S230) of acquiring a high-resolution image. For example, referring to FIG. 2E, predetermined templates may be respectively matched with the plurality of reconstructed magnetic particle-target antigen complexes 218, distributed in the detection regions 211 in the high-resolution image 232, recognized by an align key pattern in the step (S240) of counting the plurality of target substances. Next, magnetic particle-target antigen complexes 219 matched with the templates may be counted, thereby obtaining quantitative analysis results of the magnetic particle-target antigen complexes 214, more particularly the target antigens 214(b).

Hereinafter, a method of quantitatively analyzing a target substance according to another embodiment of the present invention is described with reference to FIGS. 2F to 2I. Here, reference numerals used in FIGS. 1A to 1I and FIGS. 2A to 2E are used to refer to components for convenience of description.

Before the step (S210) of irradiating a biochip with light in the method of quantitatively analyzing a target substance according to an embodiment of the present invention, electromagnetic force may be applied to the detection channel through the electromagnetic force applicators 142, previously disposed to correspond to the detection channel, so as to capture the magnetic particle-target substance complexes 214.

Figure 2F:
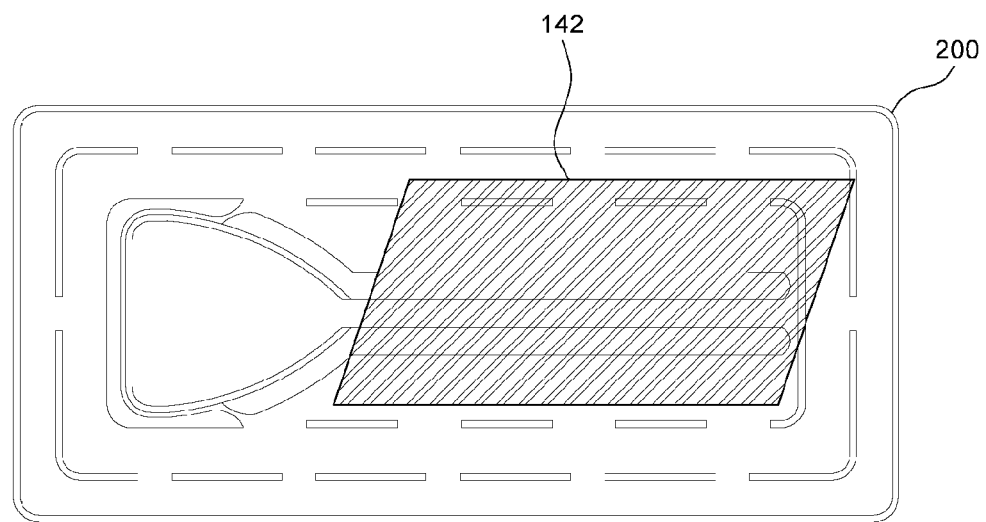
FIG. 2F is a plan view illustrating an electromagnetic force applicator of a device for quantitatively analyzing a target substance according to an embodiment of the present invention and a biochip disposed to correspond to the electromagnetic force applicator so as to describe a step of applying electromagnetic force in a method of quantitatively analyzing a target substance according to an embodiment of the present invention.

Referring to FIG. 2F, the electromagnetic force applicator 142 for the detection channel 210 disposed on the detection channel 210 of the biochip 200 may be an electromagnet with a single structure configured such that electromagnetic force is applied to all surfaces of the detection channel 210. However, the structure of the electromagnetic force applicator 142 for the detection channel is not limited to the illustrated shape, and may be varied so long as electromagnetic force can be optionally applied. For example, when the electromagnetic force applicator 142 for the detection channel is a polyhedron, a magnetically controlled circular gradient may be formed to prevent the concentration of magnetic force to each corner. When such a circular gradient is formed in the electromagnetic force applicator 142 for the detection channel, the magnetic particle-target antigen complexes 214 may be induced to uniformly flow in the detection channel 210.

Referring to FIG. 2G(a), an antibody 213 to be subjected to an immune response with the magnetic particle-target antigen complexes 214 is immobilized in the plurality of holes 212 of the detection channel 210. When electromagnetic force is applied to the electromagnetic force applicators 142 for a detection channel corresponding to a lower surface of the detection channel 210 (electromagnet on), the magnetic particles 214(a) and the magnetic particle-target antigen complexes 214 may move toward the lower surface. Here, the magnetic field strength of the electromagnetic force applicators 142 for a detection channel corresponding to the lower surface may be 20 to 32 mT. As a result of application of electromagnetic force to the electromagnetic force applicators 142 for a detection channel corresponding to the lower surface, antigen-antibody reaction efficiency between the magnetic particle-target antigen complexes 214 and the antibody 213 increases, so that the magnetic particle-target antigen complexes 214 may be captured in the holes 212. Meanwhile, due to the application of electromagnetic force to the electromagnetic force applicators 142 for a detection channel corresponding to the lower surface, non-specific complexes 215 formed by a non-specific antigen-antibody reaction between the magnetic particles 214(*a*) and the target antigens 214(*b*) may be captured in the holes 212.

Referring to FIG. 2G(b), the electromagnetic force applicators 142 for a detection channel, which correspond to the lower surface and to which magnetic force has been applied, may lose electromagnetic force (electromagnet off), and magnetic force may only be applied to the electromagnetic force applicators 142 for a detection channel corresponding to the upper surface (electromagnet on). Here, the magnetic field strength of the electromagnetic force applicators 142 for a detection channel corresponding to the upper surface may be 32 to 39 mT. As a result of the application of electromagnetic force to the electromagnetic force applicators 142 for a detection channel corresponding to the upper surface, the magnetic particles 214(*a*), which have not been subjected to an antigen-antibody reaction with the target antigens 214(*b*), and the non-specific complexes 215 may move toward the upper surface. Accordingly, the magnetic particle-target antigen complexes 214 captured by the antigen-antibody reaction with the antibody 213 only remain in the holes 212. That is, under a condition wherein electromagnetic force is applied to the electromagnetic force applicators 142 for a detection channel corresponding to the upper surface, the magnetic particles 214(*a*), the non-specific complexes 215, and the magnetic particle-target antigen complexes 214 may be detected in the detection channel 210.

Referring to FIG. 2G(c), as the electromagnetic force applicators 142 for a detection channel, which correspond to the upper surface and to which magnetic force has been applied, lose electromagnetic force (electromagnet off), all of the electromagnetic force applicators 142 for a detection channel corresponding to the upper and lower surfaces lose magnetic force (electromagnet off). As a result, the magnetic particles 214(*a*), which have not been subjected to an antigen-antibody reaction with the target antigens 214(*b*) having moved in the upper surface direction, and the non-specific complexes 215 may exit the detection channel 210. That is, under a condition where all of the electromagnetic force applicators 142 for a detection channel corresponding to the upper and lower surfaces lose magnetic force, the magnetic particle-target antigen complexes 214 may only be detected in the detection channel 210. In addition, as described above, counting may be performed by acquiring an image at a corresponding height in the holes 212 and detecting the magnetic particle-target antigen complexes 214 in the acquired image even if the antibody 213 is not a fluorescence-labeled antibody, which allows highly accurate quantitative analysis of the target antigens 214(*b*).

Before the step (S210) of irradiating a biochip with light in the method of quantitatively analyzing a target substance according to an embodiment of the present invention, electromagnetic force may be applied to the reaction channel 220 through the electromagnetic force applicators 144 arranged at a position corresponding to the reaction channel 220 such that the immune response of the magnetic particle-target substance complexes is effectively induced.

Figure 2H:
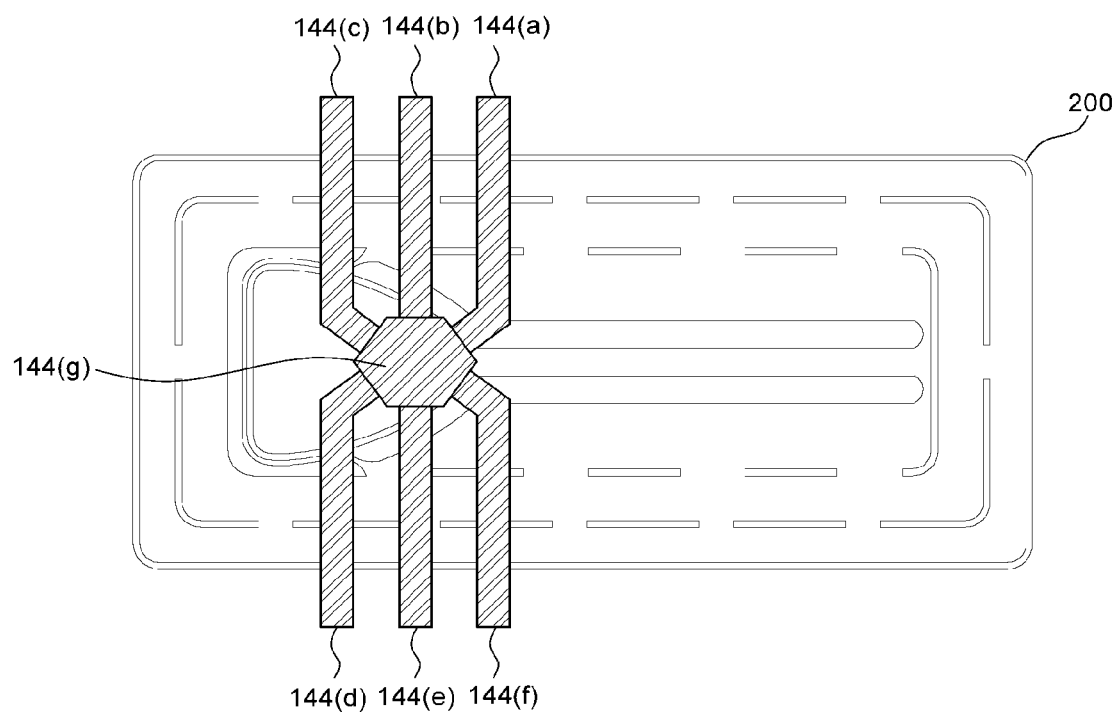
FIG. 2H is a plan view illustrating an immune response-inducing electromagnetic force applicator of a device for quantitatively analyzing a target substance according to an embodiment of the present invention and a biochip disposed to correspond to the immune response-inducing electromagnetic force applicator so as to describe a step of applying electromagnetic force in a method of quantitatively analyzing a target substance according to an embodiment of the present invention.

Referring to FIG. 2H, the electromagnetic force applicators 144 for a reaction channel which are disposed at a position corresponding to the reaction channel 220 include a core magnetic material 144 (*g*) and protruding magnetic materials 144 (*a*) to 144 (*f*) surrounding the core magnetic material 144 (*g*). However, the structure of the electromagnetic force applicators 144 for a reaction channel is not limited to the illustrated shape and may be varied so long as electromagnetic force can be optionally applied.

Referring to FIG. 2I, electromagnetic force may be applied to one protruding magnetic material pair of the plurality of protruding magnetic material pairs 144 (*a*) and 144 (*d*), 144 (*b*) and 144 (*e*), 144 (*c*) and 144 (*f*), and electromagnetic force may be applied to another protruding magnetic material pair adjacent to the electromagnetic force-applied protruding magnetic material pair. For example, electromagnetic force may only be applied to the protruding magnetic material pairs 144 (*a*) and 144 (*d*). As a result, the magnetic particles 214(*a*) may be arranged in a line at a position corresponding to the core magnetic material 136 (*g*) between the protruding magnetic material pairs 144 (*a*) and 144 (*d*) in the reaction channel 220 (FIG. 2I(a)). Next, electromagnetic force may only be applied to the protruding magnetic material pairs 144 (*b*) and 144 (*e*) or 144 (*c*) and 144 (*f*) that are adjacent to the protruding magnetic material pairs 144 (*a*) and 144 (*d*). As a result, the magnetic particles 214(*a*) may be arranged in a line at a position corresponding to the core magnetic material 136(*g*) between the protruding magnetic material pairs 144 (*b*) and 144 (*e*) or 144 (*c*) and 144 (*f*) in the reaction channel 220 (FIGS. 2I (*b*) and (*c*)). As electromagnetic force of the protruding magnetic material pairs is sequentially adjusted in such a manner, the magnetic particles 214(*a*) may rotate in the reaction channel 220. As a result, the magnetic particles 214(*a*) may be dispersed, and the antigen-antibody reaction efficiency between the target antigens 214(*b*) and the magnetic particles 214(*a*) may also increase.

Example 1: Evaluation of Method of Quantitatively Analyzing Target Substance and Quantitative Analysis Device Using Method According to Embodiment of Present Invention Hereinafter, evaluation results of the method of quantitatively analyzing a target substance and the quantitative analysis device using the method according to an embodiment of the present invention are described with reference to FIGS. 3A and 3B.

Figure 3A:
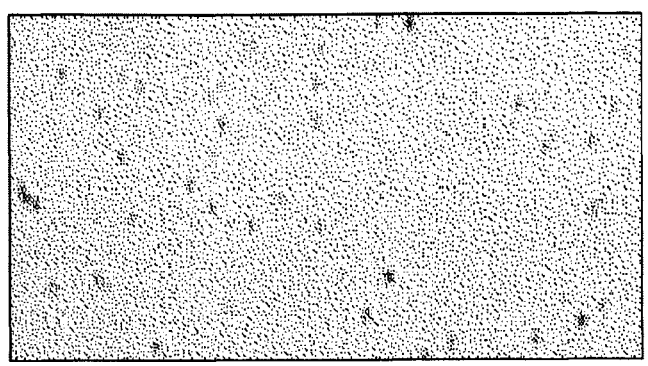
FIGS. 3A and 3B illustrate images of target substances obtained using a method of quantitatively analyzing a target substance according to an embodiment of the present invention and a quantitative analysis device using the method.
Figure 3A:
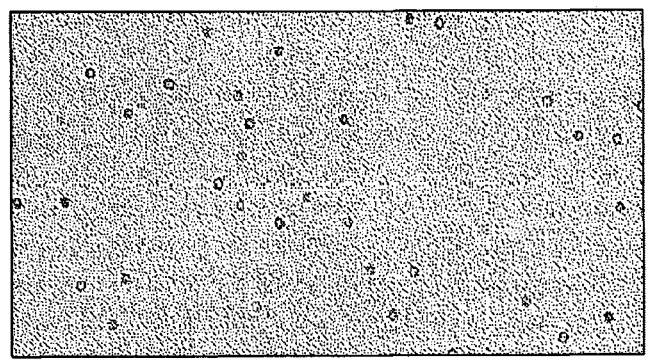
Figure 3B:
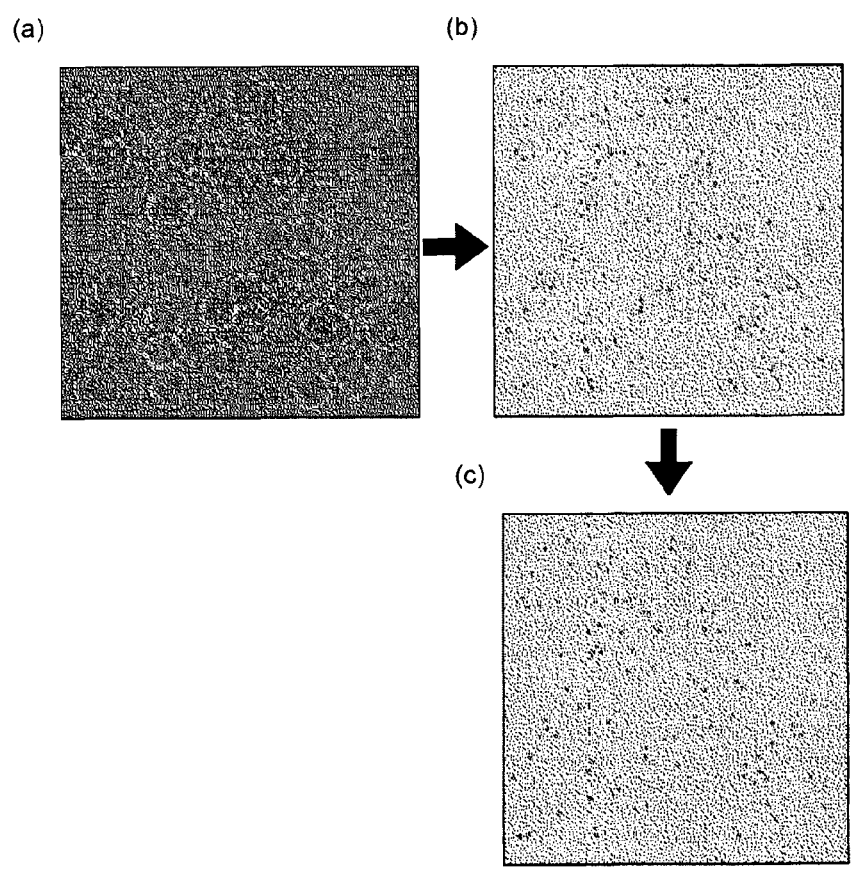

FIGS. 3A and 3B illustrate images of target substances obtained using the method of quantitatively analyzing a target substance according to an embodiment of the present invention and the quantitative analysis device using the method.

FIG. 3A illustrates a high-resolution image acquired using the method of quantitatively analyzing a target substance and the quantitative analysis device using the method according to an embodiment of the present invention. In particular, FIG. 3A (a) illustrates an image of magnetic particle-target antigen complexes in detection regions in a biochip, acquired using a quantitative analysis device excluding a pinhole aperture. FIG. 3A (b) illustrates an image of magnetic particle-target antigen complexes in detection regions in a biochip, acquired using a quantitative analysis device including a pinhole aperture. As a result, the image of FIG. 3A (b) was observed to be clearer than the image of FIG. 3A (a). Accordingly, a quantitative analysis result obtained using the quantitative analysis device including a pinhole aperture may be more reliable than in the case excluding the pinhole aperture.

FIG. 3B illustrates a procedure of acquiring a high-resolution image using the method of quantitatively analyzing a target substance and the quantitative analysis device using the method according to an embodiment of the present invention. In particular, FIG. 3B (a) illustrates one image of a plurality of low-resolution shadow images of magnetic particle-target antigen complexes in a detection region in a biochip. Based on such an image, reinterpretation was performed according to the procedure of the method of quantitatively analyzing a target substance of the present invention. As a result, a high-resolution image of the target substance was acquired as shown in FIG. 3B (b). In the high-resolution image, particle-target antigen complexes reconstructed based on the plurality of low-resolution shadow images are clearly observed. Further, the high-resolution image of FIG. 3B (c) in which a diffraction pattern has been removed according to the procedure of the method of quantitatively analyzing a target substance of the present invention may be used to provide a highly reliable quantitative analysis result of the target substance.

Figure 3C:
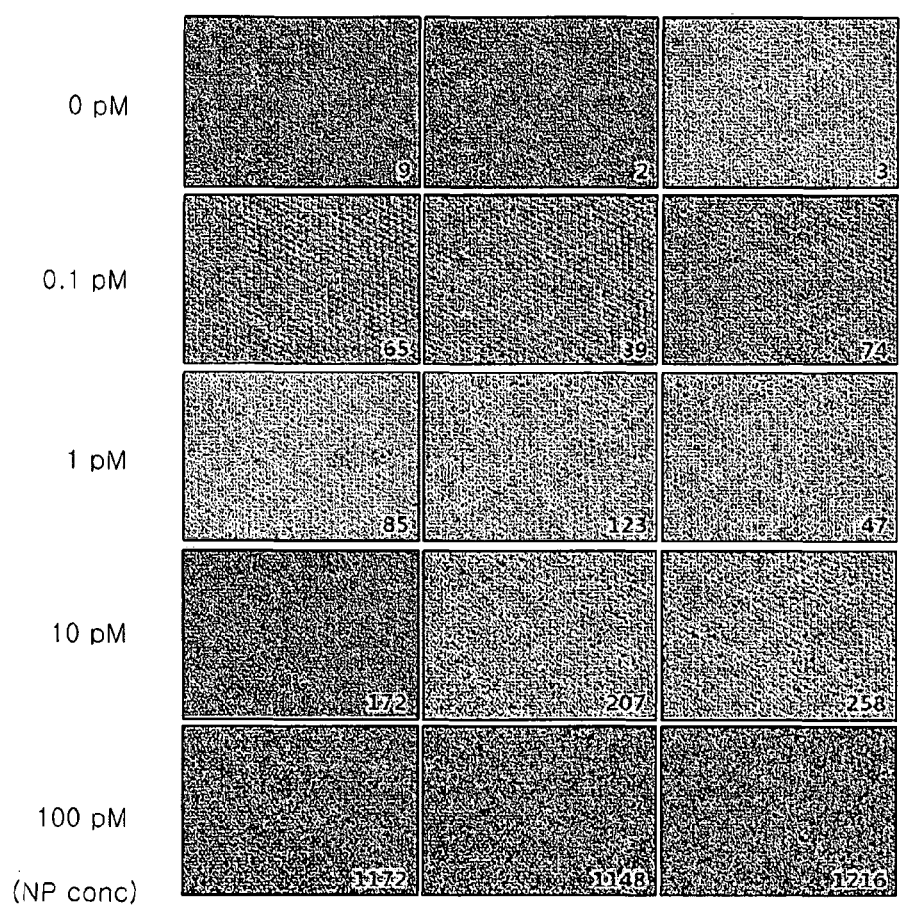
FIGS. 3C and 3D illustrate evaluation results of a method of quantitatively analyzing a target substance and a quantitative analysis device using the method according to an embodiment of the present invention.
Figure 3D:
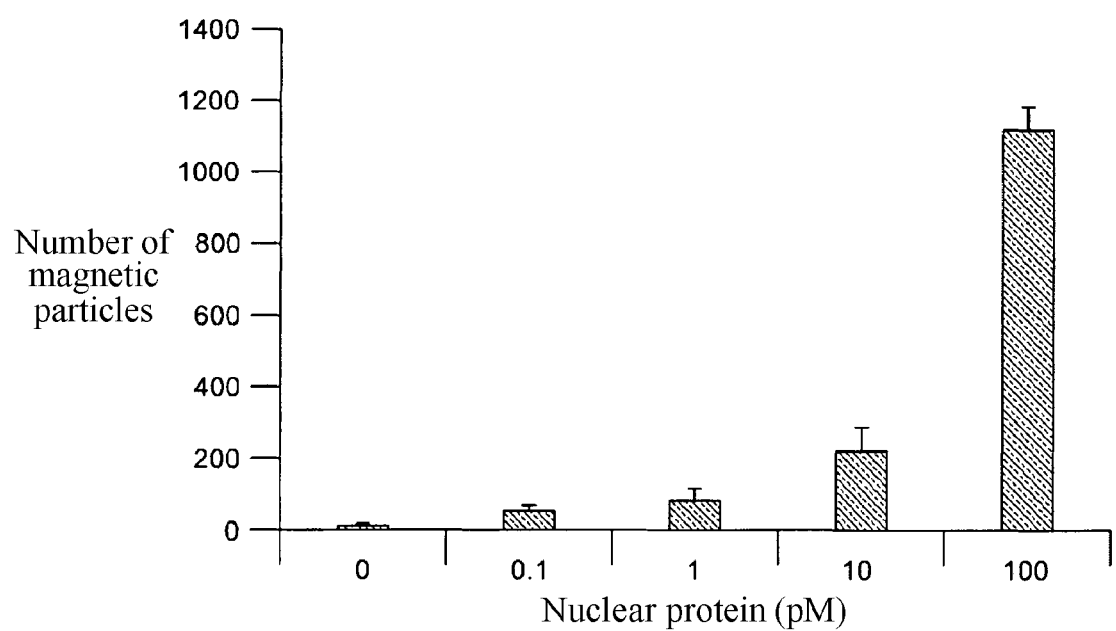

FIGS. 3C and 3D illustrate evaluation results of a method of quantitatively analyzing a target substance and a quantitative analysis device using the method according to an embodiment of the present invention.

In this evaluation, a nuclear protein of influenza A virus was set as a detection target antigen, and five repetitive experiments were performed at five concentrations. In particular, the five concentrations of the nuclear protein of influenza A virus used for the evaluation were 0 pM, 0.1 pM, 1 pM, 10 pM and 100 pM.

FIG. 3C illustrates images of some detection regions in a biochip.

In a detection channel to which the nuclear protein of influenza A virus was not added, 9, 2, 3, 2 and 15 magnetic particles were observed for each repeated experiment. Such particle numbers may represent the number of magnetic particles that did not exit the detection channel according to the magnetic control of the electromagnet.

In a detection channel to which the nuclear protein of influenza A virus was added at a concentration of 0.1 pM, 65, 39, 74, 62 and 63 magnetic particles were observed for each repeated experiment. In addition, 85, 123, 47, 78 and 98 magnetic particles were observed for each repeated experiment in a detection channel to which the nuclear protein of influenza A virus was added at a concentration of 1 pM, and 172, 207, 258, 206 and 187 magnetic particles were observed for each repeated experiment in a detection channel to which the nuclear protein of influenza A virus was added at a concentration of 10 pM. Finally, 1172, 1148, 1216, 1064 and 1087 magnetic particles were observed for each repeated experiment in a detection channel to which the nuclear protein of influenza A virus was added at a concentration of 100 pM. Here, most of the magnetic particles constituting the immune complexes observed in the detection channels to which the nuclear protein of influenza A virus was added at the concentrations of 0.1 pM, 1 pM, 10 pM and 100 pM was confirmed as being captured in the wells.

FIG. 3D is a graph illustrating the number of magnetic particles dependent upon concentration increase of the added influenza A virus nuclear protein. As a result, it was confirmed that the number of detected magnetic particles increases proportional to an increase in the concentration of the nuclear protein of influenza A virus.

As shown in Example 1, the method of quantitatively analyzing a target substance and the quantitative analysis device using the method according to an embodiment of the present invention use a CMOS image sensor, thereby being capable of providing rapid and accurate quantitative analysis for target substances detected in a biochip.

Further, in the method of quantitatively analyzing a target substance and the quantitative analysis device using the method according to an embodiment of the present invention, target substances are counted based on a high-resolution image acquired by reconstructing a plurality of low-resolution images, thereby being capable of providing highly accurate quantitative analysis.

In addition, by using the method of quantitatively analyzing a target substance and the quantitative analysis device using the method according to an embodiment of the present invention, the number of magnetic particles can be accurately counted even in a biochip excluding a fluorescence-labeled antibody, thereby being capable of providing indirect quantitative analysis for a target antigen.

Although the embodiments of the present invention have been described in more detail with reference to the accompanying drawings, the present invention is not limited to the embodiments, and may be modified into various forms without departing from the technical spirit of the present invention. Thus, the embodiments disclosed in the present invention are not intended to limit the technical idea of the present invention but to describe the present invention, and the scope of the technical idea of the present invention is not limited by the embodiments. Therefore, it should be understood that the embodiments described above are exemplary in all respects and not restrictive. The protection scope of the present invention should be interpreted by the following claims, and all technical ideas within the equivalent scope should be interpreted as being included in the scope of the present invention.

The invention claimed is:

1. A device for quantitatively analyzing a target substance, the device comprising:
   a light irradiator comprising a plurality of light emitting devices and configured to irradiate a biochip, which comprises a plurality of target substances excluding a fluorescence-labeled material, with light;
   an image sensor configured to correspond to at least a portion of the light-irradiated biochip and acquire a plurality of shadow images for each of the plurality of target substances that are generated by irradiating with light at different angles by the plurality of light emitting devices of the light irradiator; and
   a processor configured to acquire a reconstructed image for each of the plurality of target substances based on the plurality of shadow images, and count the plurality of target substances based on the reconstructed image for each of the plurality of target substances,
   wherein the biochip includes a reaction channel and a detection channel connected to the reaction channel,
   wherein the plurality of target substances include a plurality of magnetic particle-target antigen complexes,
   wherein the device further comprises:
   a plurality of magnetic force applicators for the reaction channel which are disposed at a position corresponding to the reaction channel, and
   a plurality of magnetic force applicators for the detection channel which are disposed at a position corresponding to the detection channel,
   wherein the plurality of magnetic force applicators for the reaction channel include a core magnetic material and a plurality of magnetic material pairs protruding from the core magnetic material and surrounding the core magnetic material,
   wherein the plurality of magnetic material pairs include a first magnetic material pair protruding from the core magnetic material, a second magnetic material pair protruding from the core magnetic material and adjacent to the first magnetic material pair, and a third magnetic material pair protruding from the core magnetic material and adjacent to the second magnetic material pair, and wherein the plurality of magnetic force applicators for the reaction channel are configured to sequentially apply electromagnetic force to the first magnetic material pair, the second magnetic material pair and the third magnetic material pair so that magnetic particles rotate in the reaction channel.

2. The device according to claim 1, wherein the image sensor is a CMOS image sensor, and the processor is configured to obtain the plurality of shadow images through the CMOS image sensor, acquire multilayer images of each of the plurality of target substances reconstructed based on at least one of a pixel value of each of the plurality of shadow images, a wavelength of the light and the different angles, a distance between the CMOS image sensor and the biochip, and a phase value of each of the plurality of target substances, and count the plurality of target substances based on the multilayer images.

3. The device according to claim 1, wherein each of the plurality of magnetic force applicators for the detection channel is disposed at an upper or lower part or upper and lower parts of the biochip.

4. The device according to claim 3, wherein each of the plurality of magnetic force applicators for the detection channel is a movable electromagnet or a transparent PCB electromagnet.

5. The device according to claim 3, wherein each of the plurality of magnetic force applicators for the reaction channel is disposed at an upper or lower part or upper and lower parts of the biochip.

6. The device according to claim 1, wherein the light irradiator comprises a pinhole aperture to emit isotropic light, wherein the pinhole aperture has a diameter of 0.5 to 2.5 µm.

7. The device according to claim 6, wherein the light irradiator further comprises a wavelength filter.

8. The device according to claim 1, wherein the light irradiator is disposed at an interval of 30 to 150 mm from the biochip, and the image sensor is disposed at an interval of 0.02 to 3 mm from the biochip.

9. The device according to claim 8, wherein, when the light irradiator is disposed at an interval of 30 to 150 mm from the biochip and the image sensor is disposed at an interval of 0.02 to 3 mm from the biochip, a resolution of the high-resolution image is 0.3 to 0.7 µm.

* * * * *